(12) United States Patent
Powell, Jr.

(10) Patent No.: US 6,209,550 B1
(45) Date of Patent: Apr. 3, 2001

(54) FLOSSING TOOL

(76) Inventor: Walter J. Powell, Jr., 6825 Hwy. O, Hartford, WI (US) 53027

( * ) Notice: Subject to any disclaimer, the term of this patent is extended or adjusted under 35 U.S.C. 154(b) by 0 days.

(21) Appl. No.: 09/597,065

(22) Filed: Jun. 20, 2000

(51) Int. Cl.$^7$ .................................................. A61C 15/04
(52) U.S. Cl. ............................................................ 132/323
(58) Field of Search ...................... 433/141; 132/323–327

(56) References Cited

U.S. PATENT DOCUMENTS

| | | | |
|---|---|---|---|
| 3,850,182 | 11/1974 | Clark, Jr. ............................. | 132/92 R |
| 5,029,593 | 7/1991 | Huttunen .............................. | 132/323 |
| 5,197,498 | * 3/1993 | Stewart ................................ | 132/323 |
| 5,692,532 | 12/1997 | Gabrovsek ........................... | 132/325 |
| 5,816,271 | * 10/1998 | Urso .................................... | 132/325 |
| 5,860,435 | 1/1999 | Hippensteel ......................... | 132/325 |

\* cited by examiner

Primary Examiner—Nicholas D. Lucchesi
(74) Attorney, Agent, or Firm—Donald J. Ersler

(57) ABSTRACT

A flossing tool includes a handle, first and second arms, first and second retention pads, a supply of floss string, and a cutting notch. The handle is fabricated with a handle cavity to store the supply of floss string. The first and second arms extend outward from each other and from a first end of the handle in a U-shape. The first arm has a first arm cavity and the second arm preferably has a second arm cavity. Each arm preferably has an upward curvature along its length. A first retention pad is formed on a first end of the first arm and a second retention pad is formed on a second end of a second arm. A deep groove is formed around the periphery of the junction between each retention pad and a first end of each arm. A string hole is preferably formed adjacent the first retention pad. An end of the floss string is inserted through the string hole. The string hole is located adjacent the first retention pad to reduce the amount of dexterity required to wrap the floss string around the deep groove on the first arm. The cutting notch is located on a second end of the handle.

19 Claims, 3 Drawing Sheets

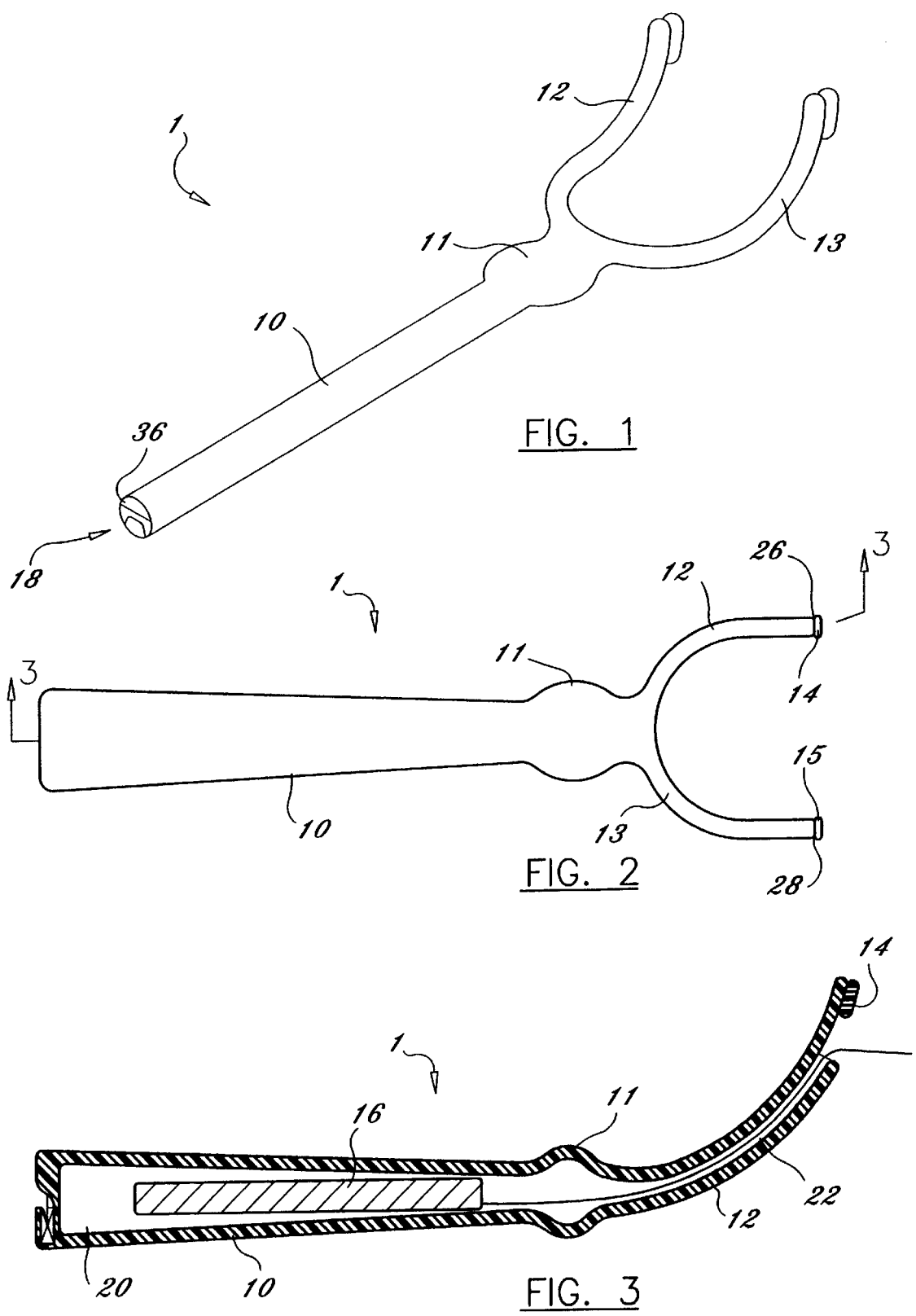

FLOSSING TOOL

BACKGROUND OF THE INVENTION

1. Field of the Invention

The present invention relates generally to devices for flossing teeth and more specifically to a flossing tool which is designed to reduce the amount effort required to attach floss string to the flossing tool.

2. Discussion of the Prior Art

Currently there are numerous tools for flossing teeth. However, many of the flossing tools have one or more drawbacks. Some of the drawbacks include complicated designs which are expensive to manufacture; require a relatively high amount of dexterity to wrap the floss string; and have a tool that is difficult to manipulate.

Accordingly, there is a clearly felt need in the art for a flossing tool which is inexpensive to manufacture, does not require a high amount of dexterity to wrap the floss string, and is not difficult to use.

SUMMARY OF THE INVENTION

The present invention provides a flossing tool which is inexpensive to manufacture and does not require a high amount of dexterity to use. The flossing tool includes a handle, first and, second arms, first and second retention pads, a supply of floss string, and a cutting notch. The handle is fabricated with a handle cavity to store the supply of floss string. The first and second arms extend from a first end of the handle and outward from each other in preferably a U-shape. The first arm has a first arm cavity and the second arm preferably has a second arm cavity. Each arm preferably has an upward curvature along its length. A first retention pad is formed on a first end of the first arm and a second retention pad is formed on a first end of the second arm.

A deep groove is formed around the periphery of the junction between each retention pad and a first end of each arm. A string hole is preferably formed adjacent the first retention pad. An end of the floss string is inserted through the string hole. The string hole is preferably located adjacent the first retention pad to reduce the amount of dexterity required to wrap the floss string around the deep groove on the first arm. The cutting notch is located on a second end of the handle. After a length of floss string has been used, it may be cut off on the cutting notch.

Accordingly, it is an object of the present invention to provide a flossing tool which is inexpensive to manufacture.

It is a further object of the present invention to provide a flossing tool which does not require a high amount of dexterity to wrap the floss string.

Finally, it is another object of the present invention to provide a flossing tool which is easy to use.

These and additional objects, advantages, features and benefits of the present invention will become apparent from the following specification.

BRIEF DESCRIPTION OF THE DRAWINGS

FIG. 1 is a perspective view of a flossing tool in accordance with the present invention.

FIG. 2 is a top view of a flossing tool in accordance with the present invention.

FIG. 3 is a side cross-sectional view of a flossing tool in accordance with the present invention.

DETAILED DESCRIPTION OF THE PREFERRED EMBODIMENTS

Figure 3A:
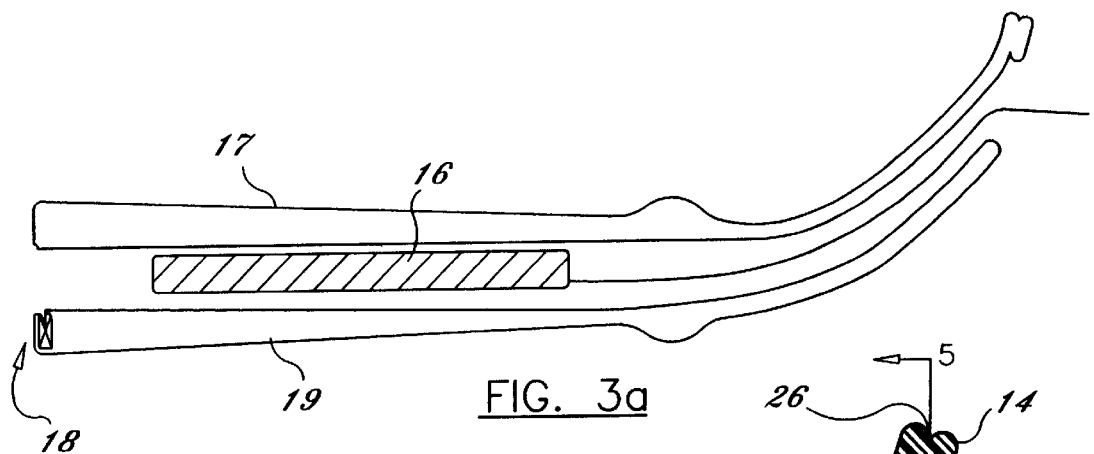
FIG. 3a is an exploded side view of a flossing tool fabricated from two pieces in accordance with the present invention.

With reference now to the drawings, and particularly to FIG. 1, there is shown a perspective view of a flossing tool 1. With reference to FIGS. 2–4, the flossing tool 1 includes a handle 10, first arm 12, second arm 13, first retention pad 14, second retention pad 15, supply of floss string 16, and cutting notch 18. The handle 10 is fabricated with a handle cavity 20 to store the supply of floss string 16. A grip 11 is preferably disposed on the first end of the handle 10. The first and second arms extend outward from a first end of the handle 10 and from each other in preferably a U-shape. The first arm 12 has a first arm cavity 22 which communicates with the handle cavity 20 to allow flossing string 16 to flow through a string hole 24. The second arm 13 preferably has a second arm cavity for ease of manufacturability. With reference to FIG. 3, both arms preferably have an upward curvature along their lengths relative to the top of the handle 10 to reduce the amount of dexterity required to manipulate thereof during use.

Figure 4:
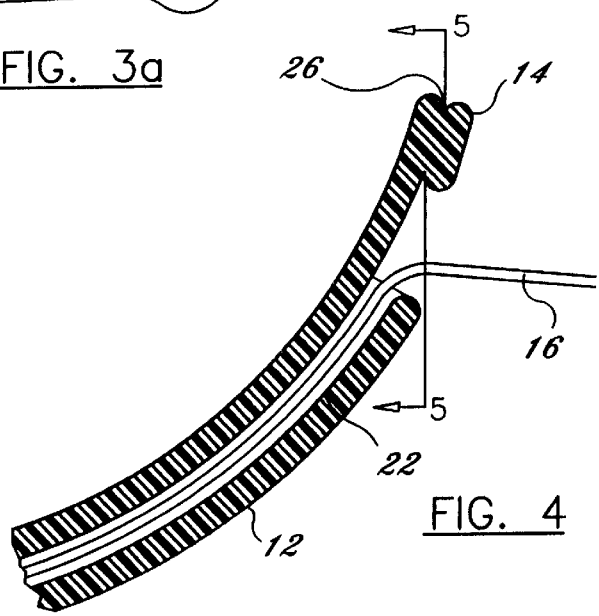
FIG. 4 is an enlarged cross-sectional side view of a first end of an arm of a flossing tool in accordance with the present invention.

With reference to FIG. 3a, the flossing tool 1 is preferably fabricated from a first half 17 and a second half 19. The use of two halves makes it possible for the handle cavity 20 to be formed in the handle 10 and the first arm cavity 22 to be formed in the first arm 12. The first and second halves are preferably fabricated from a molded plastic. If molded plastic is used, the halves are assembled to each other using glue, sonic welding, or any other suitable assembly process. Preferably, the plastic is a type which is flexible enough to allow the first and second arms to be bent toward each other such that they touch. The flexibility of the first and second arms allows the flossing tool 1 to be manipulated in the mouth more easily.

A first retention pad 14 is formed on a first end of the first arm 12. A first deep groove 26 is formed around the periphery of the junction between the first retention pad 14 and the first end of the first arm 12. A second retention pad 15 is formed on a first end of the second arm 13. A second deep groove 28 is formed around the periphery of the junction between the second retention pad 15 and a first end of the second arm 13. The first retention pad 14 and first arm 12 are preferably a single molded piece. The second retention pad 15 and second arm 13 are also preferably a single molded piece. It is also possible to attach the first retention pad 14 to the first arm 12 and attach the second retention 15 to the second arm 13 with any suitable assembly process.

Figure 4A:
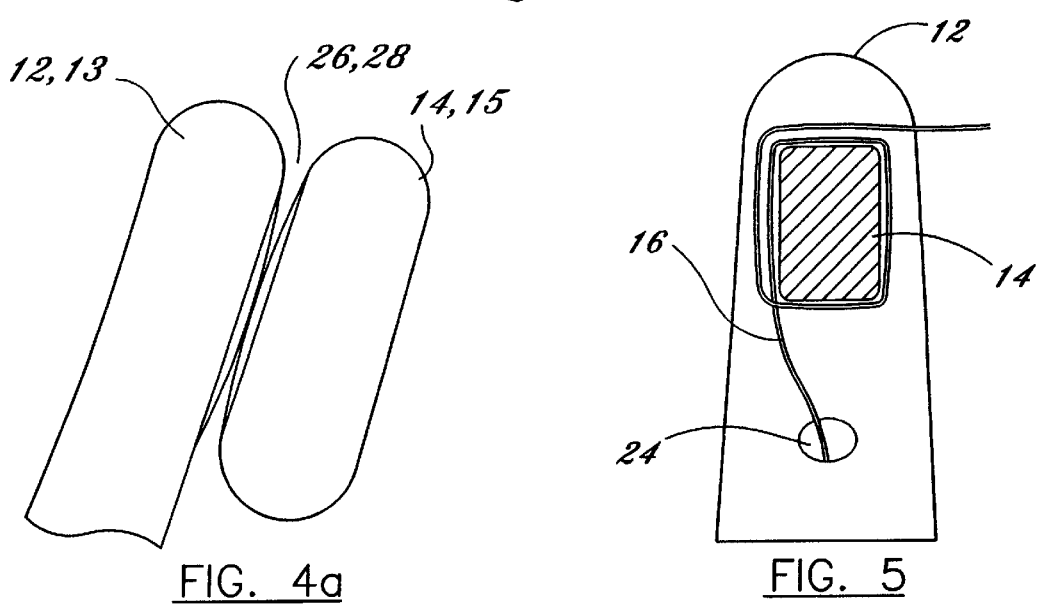
FIG. 4a is an enlarged side view of the junction between a first end of a arm and a retention pad of a flossing tool in accordance with the present invention.

FIG. 4a shows an enlarged view of the junction between the first retention pad 14 and the first end of the first arm 12 or the junction between the second retention pad 15 and the first end of the second arm 13. The bottom of the first and second deep grooves are less than the diameter of the floss 16 such that the floss is securely pinched at the bottom of the first and second deep grooves.

Figure 5:
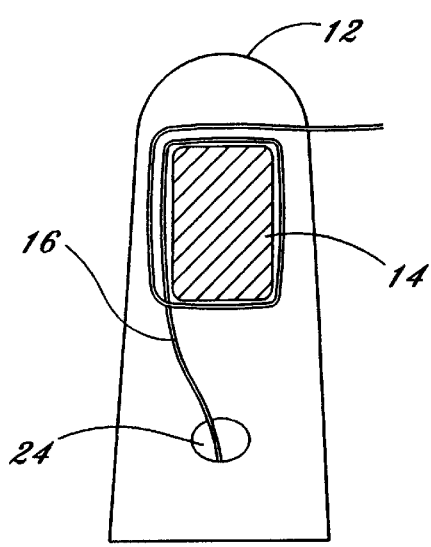
FIG. 5 is an enlarged cross-section of a deep groove of a retention pad of a flossing tool in accordance with the present invention.

With reference to FIG. 5, the shape at the bottom of the first and second deep grooves are preferably rectangular with round corners. The rectangular shape makes it more difficult for the floss string 16 to be pulled out of the deep groove 26. The round corners prevent the floss 16 from being sheared off in the first and second deep grooves. The string hole 24 is preferably formed adjacent the first retention pad 14. An end of the floss string 16 is inserted through the string hole 24. The string hole 24 is preferably located adjacent the first retention pad 14 to reduce the amount of dexterity required to wrap the floss string 16 around the first deep groove 26.

Figure 6:
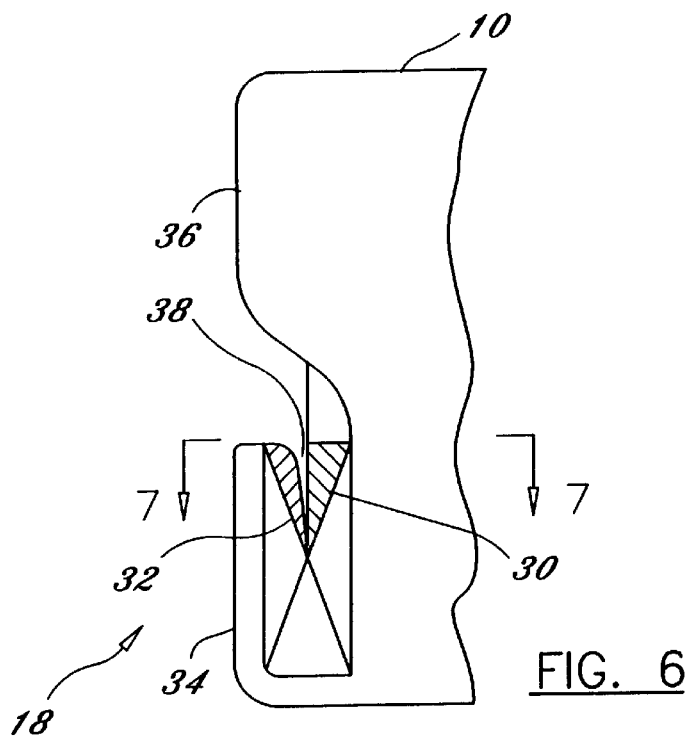
FIG. 6 is an enlarged side view of a cutting notch of a flossing tool in accordance with the present invention.
Figure 7:
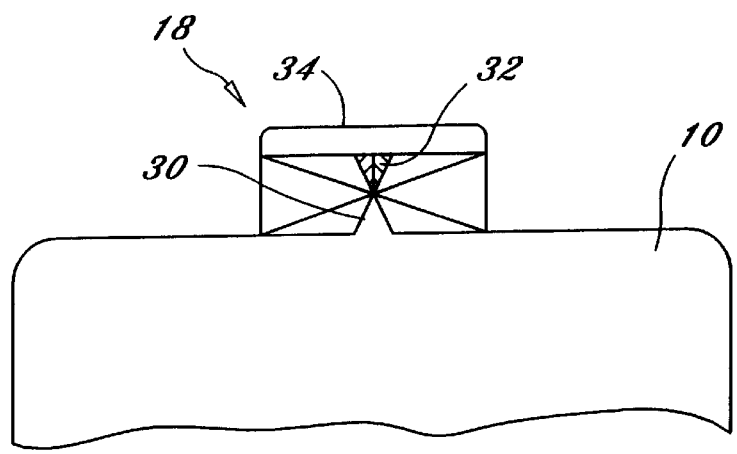
FIG. 7 is an enlarged end view of a cutting notch of a flossing tool in accordance with the present invention.
Figure 8:
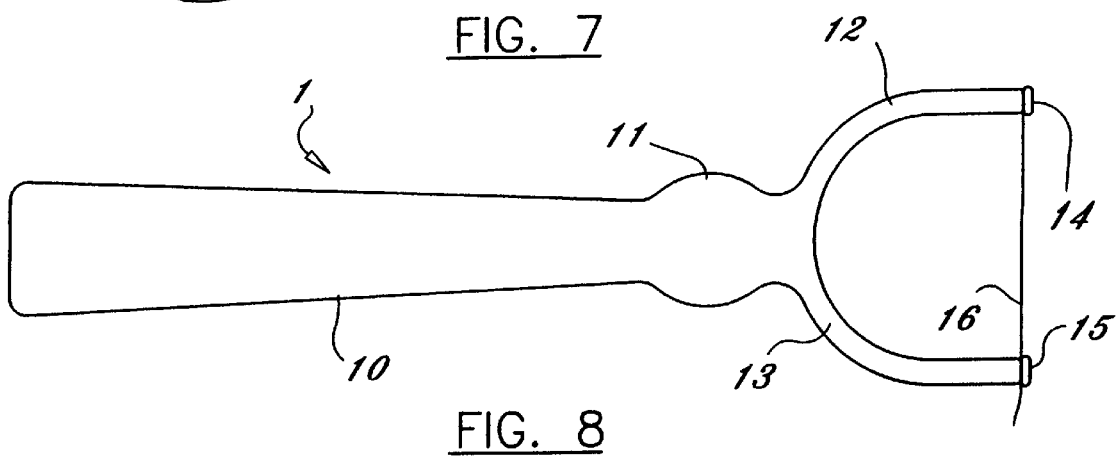
FIG. 8 is a top view of a flossing tool with floss string attached thereto in accordance with the present invention.

With reference to FIG. 6, the cutting notch 18 is located on a second end of the handle 10. The cutting notch 18 preferably includes a first knife edge 30 and a second knife edge 32. With reference to FIG. 7, the first and second knife edges have a V-shaped cross-section. A raised area 36 is formed on the second end of the handle 10 adjacent the cutting notch 18 to prevent possible injury to user from accidently scraping the cutting notch 18. The first knife edge 30 is formed on the second end of the handle 10. The second knife edge 32 extends from a knife ledge 34. The knife ledge 34 extends from the second end of the handle 10. The first and second knife edges are disposed to form a tapered cutting area 38.

The distance between the first and second knife edges at the opening of the tapered cutting area 38 are sufficient to facilitate insertion of a floss string 16. The first and second knife edges meet each other at the end of the tapered cutting area 38. Other devices for cutting the floss string 16 may also be used besides the cutting notch 18, such as a separate cutting device fabricated from metal and attached to the handle. After a length of floss string 16 has been used, it is cut-off on the cutting notch 18.

A preferable method of securing the floss 16 to the first and second arms follows. First, the flossing tool 1 is grasped by the dominant hand and a sufficient length of floss 16 is pulled out of the first arm 12 with the other hand. Second, the floss 16 is wrapped around the first deep groove 26 at least twice. Third, the unwrapped floss is pulled tight and wrapped around the second groove 28 at least twice.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A flossing tool comprising:

a handle having a first end and a second end;

a first arm extending outward from a first end of said handle, a second arm extending outward from a first end of said handle adjacent said first arm, said first and second arms extending away from each other;

a first retention pad extending from a first end of said first arm, a second retention pad extending from a first end of said second arm, a first deep groove being formed between said first retention pad and said first arm, a second deep groove being formed between said second retention pad and said second arm, a bottom of said deep grooves having a rectangular shaped perimeter with round corners; and a supply of floss string being contained with in said handle, said floss string exiting through a string hole in one of said arms.

2. The flossing tool of claim 1, further comprising:

said first and second arms having a curvature along their lengths relative to a top of said handle to reduce the amount of dexterity required to use said flossing tool.

3. The flossing tool of claim 1, wherein:

a bottom of said deep grooves having a width which is less than the diameter of said floss such that said floss is securely pinched at said bottom of said deep grooves.

4. The flossing tool of claim 1, wherein:

said string hole being located adjacent one of said retention pads to reduce the amount of dexterity required to wrap said floss string around one of said deep grooves.

5. The flossing tool of claim 1, wherein:

a cutting notch being disposed on said second end of said handle.

6. The flossing tool of claim 1, further comprising:

a grip being disposed on a first end of said handle.

7. The flossing tool of claim 1 wherein:

said flossing tool being fabricated from two halves.

8. A flossing tool comprising:

a handle having a first end and a second end;

a first arm extending outward from a first end of said handle, a second arm extending outward from a first end of said handle adjacent said first arm, said first and second arms extending away from each other;

a first retention pad extending from a first end of said first arm, a second retention pad extending from a first end of said second arm, a first deep groove being formed between said first retention pad and said first end, a second deep groove being formed between said second retention pad and said second end, a bottom of said deep grooves having a rectangular shaped perimeter with round corners; and a supply of floss string being contained with in said handle, said floss string exiting through a string hole in said first arm.

9. The flossing tool of claim 8, further comprising:

said first and second arms having a curvature along their lengths relative to a top of said handle to reduce the amount of dexterity required to use said flossing tool.

10. The flossing tool of claim 8, wherein:

a bottom of said deep grooves having a width which is less than the diameter of said floss such that said floss is securely pinched at said bottom of said deep grooves.

11. The flossing tool of claim 8, wherein:

said string hole being located adjacent said first retention pad to reduce the amount of dexterity required to wrap said floss string around said first deep groove.

12. The flossing tool of claim 8, wherein:

a cutting notch being disposed on said second end of said handle.

13. The flossing tool of claim 8, further comprising:

a grip being disposed on a first end of said handle.

14. The flossing tool of claim 8, wherein:

said flossing tool being fabricated from two halves.

15. A flossing tool comprising:

a handle having a first end and a second end;

a first arm extending outward from a first end of said handle, a second arm extending outward from a first end of said handle adjacent said first arm, said first and second arms extending away from each other;

a first retention pad extending from a first end of said first arm, a second retention pad extending from a first end of said second arm, a first deep groove being formed between said first retention pad and said first arm, a second deep groove being formed between said second retention pad and said second end, a bottom of said deep grooves having a rectangular shaped perimeter with round corners, a bottom of said deep grooves having a width which is less than the diameter of said floss such that said floss is securely pinched at said bottom of said deep grooves; and a supply of floss string being contained with in said handle, said floss string exiting through a string hole in said first arm, said string hole being located adjacent said first retention pad to reduce the amount of dexterity required to grap said floss string around said first deep groove.

16. The flossing tool of claim 15, wherein:

said first and second arms having a curvature along their lengths relative to a top of said handle to reduce the amount of dexterity required to use said flossing tool.

17. The flossing tool of claim 15, wherein:

a cutting notch being disposed on said second end of said handle.

18. The flossing tool of claim 15, further comprising:

a grip being disposed on a first end of said handle.

19. The flossing tool of claim 15, wherein:

said flossing tool being fabricated from two halves.

\* \* \* \* \*